United States Patent [19]
Gage et al.

[11] Patent Number: 6,033,408
[45] Date of Patent: Mar. 7, 2000

[54] RESECTING TOOL FOR MAGNETIC FIELD ENVIRONMENT

[75] Inventors: Gary B. Gage; Ray Umber, both of Arlington; Glenn T. Carlson, Keller; Townesend R. Scantlebury, Arlington, all of Tex.

[73] Assignee: Midas Rex, L.P., Fort Worth, Tex.

[21] Appl. No.: 09/110,729

[22] Filed: Jul. 6, 1998

Related U.S. Application Data

[63] Continuation-in-part of application No. 08/690,634, Jul. 30, 1996, Pat. No. 5,782,836.

[51] Int. Cl.[7] ................................................ A61B 17/32
[52] U.S. Cl. ........................ 606/79; 606/180; 173/218; 415/904
[58] Field of Search ............................. 606/79, 80, 180; 415/200, 216.1, 904; 173/93.5, 104, 218, 221

[56] References Cited

U.S. PATENT DOCUMENTS

| 2,734,413 | 2/1956 | Dunkelberger | 81/63.2 |
|---|---|---|---|
| 2,807,473 | 9/1957 | Kiehne | 279/279 |
| 3,472,323 | 10/1969 | Hall | 173/163 |
| 3,752,241 | 8/1973 | Bent | 173/163 |
| 4,071,029 | 1/1978 | Richmond et al. | 128/305 |
| 5,028,181 | 7/1991 | Jenkins et al. | 409/215 |
| 5,383,771 | 1/1995 | Ghode et al. | 418/15 |
| 5,439,005 | 8/1995 | Vaughn | 128/755 |
| 5,505,737 | 4/1996 | Gosselin et al. | 606/79 |

*Primary Examiner*—Michael Buiz
*Assistant Examiner*—David O. Reip

[57] ABSTRACT

A pneumatic surgical tool for cutting bone during surgical procedures includes a pneumatic motor having a rotary shaft, a resecting tool having a cutting element rotated by the motor, a chuck sleeve to surround and support the resecting tool, and anti-friction bearings for further rotatably supporting the resecting tool. The rotor and chuck sleeve are formed of an electrically nonconductive material. The resecting tool is formed of titanium. The bearings are formed of a ceramic, composite or plastic material.

14 Claims, 2 Drawing Sheets

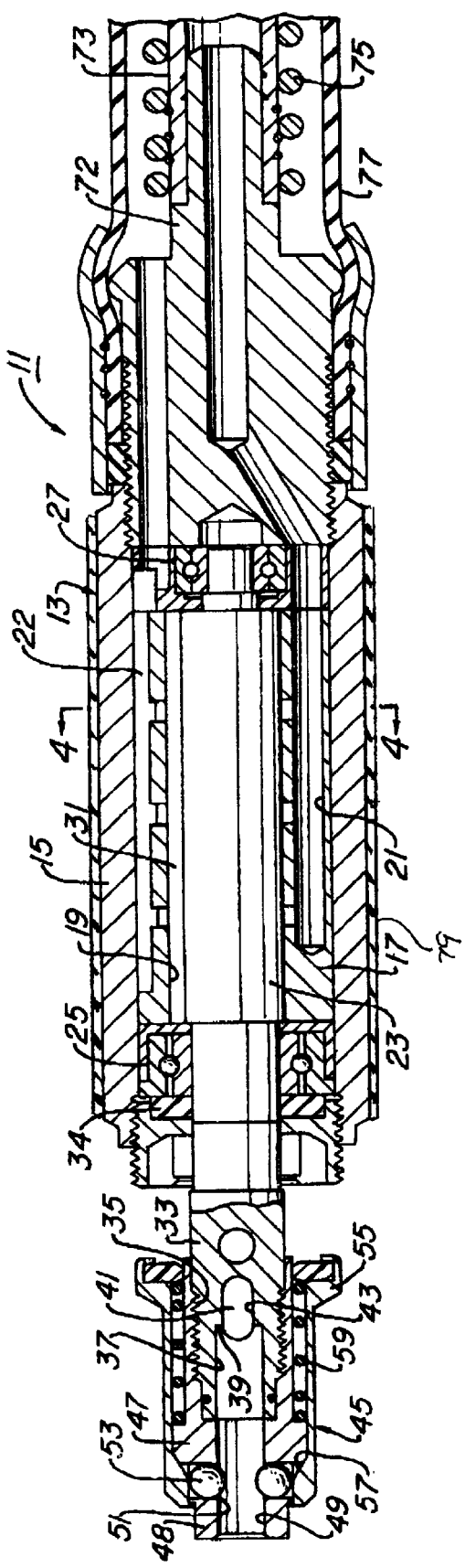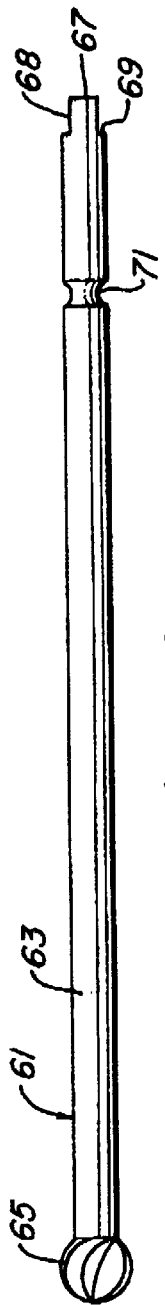

RESECTING TOOL FOR MAGNETIC FIELD ENVIRONMENT

CROSS-REFERENCE TO RELATED APPLICATION

This application is a continuation-in-part of application Ser. No. 08/690,634 filed Jul. 30, 1996, now U.S. Pat. No. 5,782,836.

TECHNICAL FIELD

The present invention relates in general to surgical instruments and, in particular, to a pneumatic resecting tool suitable for use in environments containing strong magnetic fields.

BACKGROUND ART

Surgical tools for use in the dissection of bone during surgical procedures are conventional in the art. Many such tools employ pneumatic motors to rotate the cutting element of a resecting tool. In their most basic form, such surgical instruments comprise a motor portion having a rotary shaft, a resecting tool having a cutting element, and a chuck for connecting the resecting tool to an outer end of spindle of the rotary shaft. These surgical instruments have been created from carbon steel because of the need for high material hardness and ability to withstand the wear of operating at high speeds. Also, thin hardened cases, such as titanium nitride and titanium aluminum nitride have been applied to the bore of the motor housing to reduce wear caused by the rotating vanes. In addition to steel, resecting tools in some instances have been formed to tungsten carbide.

A fairly recent diagnostic technique involves the use of magnetic resonance imaging (MRI) machines or other machines which create or utilize very high strength magnetic fields. These machines provide an image of internal organs of the human body. Surgeons may utilize the images from such machines to guide them in performing subsequent surgery. It would be advantageous to be able to perform surgery using pneumatic resecting tools while in the MRI suite. However, the resident high magnetic field will attract magnetic objects, potentially creating unguided missiles. Because of the ferrous metal in the motors, these pneumatic resecting tools are not used.

For use during MRI operations, it would be very desirable to create surgical tools using nonferrous materials that would be unaffected by magnetic fields. However, nonferrous metals such as titanium have traditionally only been used in implants and hand tools such as pliers and nippers, not in pneumatic resecting motors, which rotate at high speeds.

DISCLOSURE OF INVENTION

A pneumatic surgical tool for the resection of bone during surgical procedures is driven by a pneumatic motor housing subjected to air pressure from an outside source which enters through air inlet passages and exits through air outlet passages in the housing. A rotary shaft or rotor is located within a bore in the motor housing and has an axis parallel to and offset from an axis of the bore. The rotary shaft has a spindle or outer end extending out of the motor housing and is rotatably supported by bearings. A resecting tool with a cutting element is connected to the spindle of the rotary shaft and rotated by the motor. A chuck connects to the spindle and secures the resecting tool.

The present invention improves the conventional surgical tool by creating substantially all of the spinning components of the motor from a material which is either electrically nonconductive or resistive. One type of material for the rotor is a ceramic or composite material. The bearings are preferably formed of a ceramic, plastic or composite material. The chick sleeve may be of a plastic or composite material.

The resecting tool may be of titanium, and the housing may be either of titanium or another material which is substantially nonmagnetic. One such material is a series 300 stainless steel, fully annealed. Preferably, the bore of the housing has a thin hard metal case to increase the hardness of the tool and its resistance to wear. The thin coating is applied by known vapor deposition techniques and can be titanium nitride, titanium aluminum nitride, or titanium carbon nitride.

BRIEF DESCRIPTION OF THE DRAWINGS

FIG. 1 is a partial cross-sectional side view of a pneumatic motor for a resecting tool constructed according to the present invention.

FIG. 2 is a side elevational view of a cutting tool constructed according to the present invention and for use with the motor of FIG. 1.

BEST MODE FOR CARRYING OUT THE INVENTION

Figure 3:
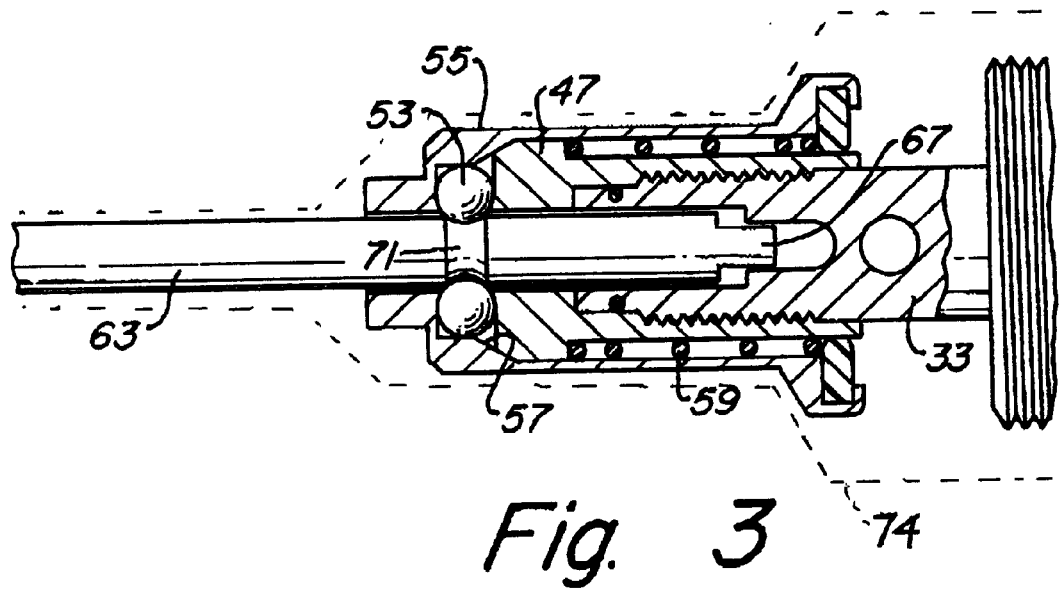
FIG. 3 is a partial cross-sectional side view of the chuck for the motor of FIG. 1, with the cutting tool of FIG. 2 secured therein.

Referring to FIG. 1, a surgical instrument 11 used for cutting bone in surgical procedures is shown. The surgical instrument 11 has a pneumatic driven motor 13 having a housing 17 surrounded by an outer sleeve 15, both formed of material which is substantially nonmagnetic. One such material is titanium. Another suitable material is series 300 stainless steel, fully annealed. Both of these materials are electrically conductive. However, as they do not rotate and are nonmagnetic, they will not be affected by the high magnetic field or the effect will be negligible. Motor housing 17 has a cylindrical bore 19. Pressurized air is supplied to bore 19 through a plurality of air inlet passages 21. Bore 19 also has a plurality of air outlet passages 22 opposite air inlet passages 21 for the discharge of pressurized air.

Figure 4:
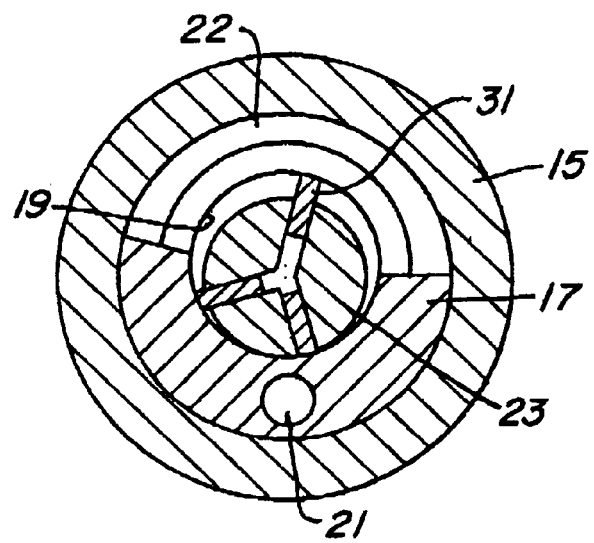
FIG. 4 is a cross-sectional view of the motor of the resecting tool of FIG. 1, taken along the line 4—4 of FIG. 1.

A rotor or rotary shaft 23 is located inside bore 19 and has an axis parallel to but offset from the axis of bore 19, as illustrated also in FIG. 4. The axis of rotor 23 is located closer to the side of bore 19 containing air inlet passages 21 and away from the side of bore 19 containing air outlet passages 22. Rotor 23 is formed of a material which is not only nonmagnetic, but also is either highly resistive or substantially nonconductive of electricity, such as a ceramic material. Another such material comprises carbon fibers which extend longitudinally and are bonded together in an epoxy resin binder. Although carbon is conductive, the nonconductive resin binder separates the fibers and reduces the conductivity through rotor 23, making the composite more resistive. Another material which would be possible for rotor 23 is zirconia.

Rotor 23 is rotatably supported in bore 19 by bearings 25, 27 which are axially spaced apart from each other. Bearings 25, 27 are preferably ball bearings formed of a ceramic material or they may be journal bearings. The ceramic material is nonelectrically conductive but brittle. Heat generated during operation could cause cracking of bearing 25, 27 if axial expansion of rotor 23 due to heat applied high axial forces to bearings 25, 27. The coefficient of expansion, however, of ceramic or carbon fiber resin is not high. Also, it is less than titanium or series 300 stainless steel. Consequently, rotor 23 will not expand more than housing 17 and thus will not place high forces and thus hoop stresses on bearings 25, 27.

As shown in FIG. 4, rotor 23 has three slots extending radially from the axis of rotor 23 and spaced 120 degrees apart from each other. A nonmetallic vane 31 is located inside each slot, and each vane 31 can slide radially inward or outward relative to the axis of rotor 23. As rotor 23 rotates inside bore 19, each vane 31 slides inward and outward such that it always remains in contact with the wall of bore 19. To avoid excessive wear, bore 19 has a hardened case of titanium nitride, titanium aluminum nitride, or titanium carbon nitride. The case is very thin, approximately 0.001 inch. The case is formed by known vapor deposition techniques. The case has a hardness in the range from about 87 to 92 Rockwell "C".

Bearings 25, 27 are located at the forward and rearward ends of housing 17 and rotatably support rotor 23. The balls and races of roller bearings 25, 27 are preferably of a nonelectrically conductive hard material, such as ceramic. Alternately, a journal or sleeve bearing of a non-magnetic plastic material may be employed.

rotor 23 has an outer end or spindle 33 which extends out of bore 19. Spindle 33 protrudes from the forward end of motor 13 and is integrally formed with rotor 23. A permanent nonmetallic seal 34 is located in the forward end of outer sleeve 15 for sealing around rotor 23 and/or the forward bearing. A nonmetallic safety seal 34 is located outside outer sleeve 15, also for sealing against leakage of oil from the interior of housing 17. Safety seal 34 is removed after each use and replaced with a new seal.

Spindle 33 has a plurality of threads 35 on its exterior. A socket 37 extends into spindle 33. Socket 37 is cylindrical and has a shoulder or base 39 that is perpendicular to the axis of rotor 23. A slot 41 extends rearward from base 39. Slot 41 is generally rectangular, having two opposed flat faces 43 which serve as torque transmitting surfaces. Faces 43 are spaced equidistant from the axis of rotor 23.

a chuck assembly 45 is secured to spindle 33. Chuck assembly 45 has an inner or chuck sleeve 47 which has internal threads that mate with threads 35. Chuck sleeve 47 is also of a material which is electrically nonconductive, such as a plastic. Chuck sleeve 47 may have a thin minimally magnetic metal or ceramic liner (not shown) for wear resistance. Inner sleeve 47 has a protruding neck 48 which has a cylindrical axial passage 49. Passage 49 aligns with and is the same diameter as cylindrical socket 37. A plurality of apertures 51 are located in neck 48. Apertures 51 extend from passage 49 to the exterior and are spaced circumferentially apart.

A ceramic ball 53 is positioned within each aperture 51. Balls 53 are capable of moving inward, protruding into passage 49 as shown, and moving outward. In the outer, released position, balls 53 are radially outward of passage 49. An outer or cam sleeve 55 is carried on inner sleeve 47. Outer sleeve 55 is capable of axial movement relative to inner sleeve 47 between a locked position shown in FIG. 1 and a released position, forward of the locked position. In the released position, a cam surface 57 on outer sleeve 55 moves forward of balls 53, allowing them to move to the released position. In the locked position shown, cam 57 retains balls 53 in the locked position. Cam sleeve 55 is also formed of an electrically nonconductive material such as a plastic, but may have a thin metal, ceramic or plastic liner. A spring 59 compressed between outer sleeve 55 and inner sleeve 47 urges outer sleeve 55 rearward to the locked position. Spring 59 is preferably formed of a nonferrous material such as beryllium copper.

Referring to FIG. 4, a resecting tool 61 is adapted to be coupled to spindle 33. Resecting tool 61 is formed of a nonferrous material, preferably titanium. Resecting tool 61 has a shaft 63 with a cutting tip 65 on its end. Cutting tip 65 may have a hardened case of titanium nitride, titanium aluminum nitride, or titanium carbon nitride. The case is very thin, approximately 0.0001 inch. The case is formed by known vapor deposition techniques in the same manner as the case on bore 19 of motor housing 17.

Resecting tool 61 also has a torque transmitting tang 67. Tang 67 is located on the axis of shaft 63, and has two flat sides 68 which face opposite each other. Tang 67 protrudes from a rearward facing shoulder 69. Tang 67 is adapted to be closely received within slot 41 (FIG. 3) with faces 68 in engagement with faces 43. A groove 71 extends circumferentially around shaft 63 for receiving balls 53.

A guide tube 74, shown by dotted lines in FIG. 3, will enclose resecting tool 63 and chuck assembly 45. Guide tube 74 secures to the threads shown at the forward end of housing 17. Guide tube 74 has a movable sleeve (not shown) which may be manually moved forward to move sleeve 55 to release tool 63. Guide tube 74 is also formed of a nonmagnetic material such as titanium or fully annealed 300 series stainless steel.

Referring to FIG. 1, motor housing 17 has a rearward end that has a mandrel 72 of the same material as motor housing 17. An inner hose 73 of elastomeric material secures to mandrel 72. A stiffener spring 75 of nonferrous material encircles inner hose 73. An outer hose 77 is secured to housing 17, defining an annular passage surrounding inner hose 73. Preferably a non-conductive autoclave survivable insulating sleeve 79 fits over sleeve 15. Sleeve 79 is an elastomer which insulates the surgeon's fingers from heat generated by motor 13.

In operation, air at about 100 psi is supplied through inner hose 73, with the air flowing through passage 21 to act against vanes 31. This causes rotor 23 to spin at a high speed. Air is exhausted through air outlet passages 22 and the annular space within outer hose 77. Rotor 23 rotates spindle 33, which in turn rotates resecting tool 61. The rotational force is transmitted by faces 43 against faces 68. Balls 53 and outer sleeve 55 retain shaft 63 against tension.

Surgical instrument 11 is capable of operating in a high strength field created by an MRI machine. Most of the motor rotating components such as the rotor 23, spindle 33, and chick 45 are electrically nonconductive, therefore avoid generating heat due to the spinning of electrical conductor sin a magnetic field. Although the nonrotating components may be of electrically conductive material such as stainless steel or titanium, these materials are essentially nonmagnetic.

While the invention has been shown in only one of is forms, it should be apparent to those skilled in the art that it is not so limited but is susceptible to various changes without departing from the scope of the invention.

We claim:

1. A surgical instrument for resecting human bone within an environment containing a strong magnetic field, comprising:

a motor housing having a bore which has an axis;

a rotor rotatably mounted in the bore on spaced apart bearings, the rotor being located on an axis parallel to and offset from the axis of the bore, the rotor having at least one slot which extends radially from the rotor axis, the rotor having an outer end which extends out of the motor housing for coupling to a resecting tool;

at least one nonmetallic vane carried slidably in the slot of the rotor and having an edge which slidingly engages the bore;

an air inlet and an air outlet passage in the motor housing for delivering air pressure to and exhausting from the bore to cause the rotor to spin; and the rotor being formed of material that is substantially nonmagnetic and electrically nonconductive so as to avoid being influenced by the magnetic field.

2. The surgical instrument according to claim 1, wherein the motor housing is formed of a metal which is substantially nonmagnetic.

3. The surgical instrument according to claim 1, further comprising a chuck sleeve mounted to the outer end of the rotor for connecting a resecting tool to the rotor, the chick sleeve being formed of a material which is substantially nonmagnetic and electrically nonconductive.

4. The surgical instrument according to claim 1, wherein the rotor is formed of a ceramic material.

5. The surgical instrument according to claim 1, wherein the rotor is formed of a carbon fiber composite.

6. The surgical instrument according to claim 1, further comprising:

a resecting tool;

a chuck sleeve mounted to the outer end of the rotor for connecting the resecting tool to the rotor, the chick sleeve and the resecting tool being formed of a material which is substantially nonmagnetic; and a guide tube secured to the motor housing and enclosing the chick sleeve, the resecting tool extending through the guide tube, the guide tube being formed of a material which is substantially nonmagnetic.

7. The surgical instrument according to claim 1, wherein the bearings are formed of a ceramic material.

8. A surgical instrument for resecting human bone within an environment containing a strong magnetic field, comprising:

a motor housing having a bore which has an axis;

a rotor rotatably mounted in the bore on spaced apart bearings, the rotor being located on an axis parallel to and offset from the axis of the bore, the rotor having a plurality of slots which extend radially from the rotor axis;

a plurality of nonmetallic vanes carried slidably in the slots, each having an edge which slidingly engages the bore;

an air inlet and air outlet passage in the motor housing for delivering air pressure to the bore to cause the rotor to spin;

the rotor having an outer end which extends out of the motor housing;

a chuck sleeve secured to the outer end of the rotor;

a guide tube secured to the motor housing and enclosing the chick sleeve;

a resecting tool having a cutting tip and a shaft end which locates within the chick sleeve for coupling to the shaft and protrudes through the guide tube;

the rotor and the chuck sleeve being formed of a resistive material so as to avoid being influenced by the magnetic field; and the motor housing, resecting tool and guide tube being formed of a metal which is substantially nonmagnetic.

9. The surgical instrument according to claim 8, wherein the rotor is formed of a carbon fiber material.

10. The surgical instrument according to claim 8, wherein the rotor is formed of a ceramic material.

11. The surgical instrument according to claim 8, wherein the bearings are formed of a material from a group consisting essentially of ceramic, plastic or composite.

12. The surgical instrument according to claim 8, wherein:

the shaft has a circumferential groove spaced axially from the flat surface on the end;

the chick sleeve has a plurality of apertures; and wherein the instrument further comprises:

a plurality of ceramic balls carried within the chick sleeve, movable between an engaged position with the groove on the shaft and a released position free of the groove; and a cam sleeve which holds the balls in the engaged position and which is axially movable relative to the chuck sleeve to allow the balls to move to the released position, the cam sleeve being formed of an electrically nonmagnetic material.

13. The surgical instrument according to claim 12, wherein the cam sleeve is formed of a substantially electrically nonconductive material.

14. A method for resecting human bone within an environment containing a strong magnetic field, comprising:

providing a rotary surgical instrument having a motor housing made of a material which is substantially nonmagnetic and having a bore which has an axis;

rotatably mounting a rotor made of material which is electrically highly resistive in the bore on spaced apart bearings on an axis parallel to and offset from the axis of the bore;

providing at least one nonmetallic sliding vane on the rotor;

mounting a chick sleeve made of an electrically highly resistive material to the outer end of the rotor;

inserting a resecting tool made of substantially nonmagnetic metal into the chick sleeve; and while the surgical instrument is locate din the magnetic field, delivering air pressure to the bore of the motor housing to cause the rotor to spin, which rotates the resecting tool, then engaging the resecting tool with the bone.

* * * * *